United States Patent
Jeon et al.

(10) Patent No.: US 11,844,646 B2
(45) Date of Patent: Dec. 19, 2023

(54) ULTRASOUND DIAGNOSIS APPARATUS AND OPERATING METHOD FOR THE SAME

(71) Applicant: SAMSUNG MEDISON CO., LTD., Hongcheon-gun (KR)

(72) Inventors: Hyunjae Jeon, Seongnam-si (KR); Dongkuk Shin, Seongnam-si (KR); Sungjin Choi, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 98 days.

(21) Appl. No.: 16/988,280

(22) Filed: Aug. 7, 2020

(65) Prior Publication Data

US 2021/0219943 A1 Jul. 22, 2021

(30) Foreign Application Priority Data

Jan. 17, 2020 (KR) .................. 10-2020-0006748

(51) Int. Cl.
*A61B 8/00* (2006.01)
*A61B 8/08* (2006.01)
*A61B 8/14* (2006.01)

(52) U.S. Cl.
CPC .............. *A61B 8/085* (2013.01); *A61B 8/145* (2013.01); *A61B 8/4494* (2013.01); *A61B 8/463* (2013.01); *A61B 8/54* (2013.01)

(58) Field of Classification Search
CPC ......... A61B 8/085; A61B 8/483; A61B 8/145; A61B 8/4494; A61B 8/463; A61B 8/54;
(Continued)

(56) References Cited

U.S. PATENT DOCUMENTS

| | | | |
|---|---|---|---|
| 6,623,432 B2 * | 9/2003 | Powers | A61B 8/0883 600/447 |
| 7,033,320 B2 | 4/2006 | Von Behren et al. | |

(Continued)

FOREIGN PATENT DOCUMENTS

| | | |
|---|---|---|
| JP | 2011010864 A | 1/2011 |
| KR | 1020110080517 A | 7/2011 |
| WO | 2020/008746 A1 | 1/2020 |

OTHER PUBLICATIONS

Krivanek et al., "Ovarian Ultrasound Image Analysis: Follicle Segmentation", Dec. 1998, IEEE Transactions on Medical Imaging, vol. 17 No. 6, pp. 935-944 (Year: 1998).*
(Continued)

*Primary Examiner* — Pascal M Bui Pho
*Assistant Examiner* — Adil Partap S Virk
(74) *Attorney, Agent, or Firm* — Sughrue Mion, PLLC

(57) ABSTRACT

An ultrasound diagnosis apparatus includes: a display; a memory storing one or more instructions; and a processor configured to execute the one or more instructions stored in the memory to: generate a plurality of ultrasound images of an object including a plurality of entities, based on echo signals received from the object; detect first and second entities among the plurality of entities in each of the plurality of ultrasound images; acquire size information regarding the detected first entity and size information regarding the detected second entity from each of the plurality of ultrasound images; and control the display to display, based on the size information regarding the first entity and the size information regarding the second entity, a first ultrasound image showing a largest size of the first entity and a second ultrasound image showing a largest size of the second entity, from among the plurality of ultrasound images.

17 Claims, 10 Drawing Sheets

(58) Field of Classification Search
CPC ... A61B 8/4427; A61B 8/0833; A61B 8/5223; A61B 8/468; A61B 8/0866; A61B 8/4405; A61B 8/467; A61B 8/465; A61B 8/5238; G01S 7/52053; G01S 15/8906
See application file for complete search history.

(56) References Cited

U.S. PATENT DOCUMENTS

| | | | |
|---|---|---|---|
| 9,679,375 | B2 | 6/2017 | Eskandari et al. |
| 10,127,654 | B2 | 11/2018 | Murphy et al. |
| 10,433,727 | B2* | 10/2019 | Canda ................... A61B 5/0035 |
| 2004/0127796 | A1* | 7/2004 | Chalana ............... A61B 8/0833 600/449 |
| 2007/0276254 | A1* | 11/2007 | Yang ....................... G06T 7/149 600/463 |
| 2009/0024032 | A1* | 1/2009 | Kato ..................... A61B 8/463 600/443 |
| 2012/0287131 | A1* | 11/2012 | Matsuzaki ............ G06T 3/0068 345/426 |
| 2014/0031691 | A1 | 1/2014 | Nagase et al. |
| 2016/0051230 | A1* | 2/2016 | Yoo ......................... A61B 8/466 600/440 |
| 2016/0063695 | A1* | 3/2016 | Lee ......................... A61B 8/463 382/131 |
| 2016/0331349 | A1* | 11/2016 | Abe ....................... A61B 5/318 |
| 2017/0103518 | A1 | 4/2017 | Murphy et al. |
| 2017/0262600 | A1 | 9/2017 | Park et al. |
| 2019/0239858 | A1 | 8/2019 | Shin |
| 2019/0374193 | A1* | 12/2019 | Ramachandran ...... A61B 8/483 |
| 2020/0205785 | A1 | 7/2020 | Jeon et al. |
| 2020/0229796 | A1* | 7/2020 | Yang .................... A61B 8/5215 |

OTHER PUBLICATIONS

Deutch et al., "Automated assessment of ovarian follicles using a novel three-dimensional ultrasound software", Nov. 2009, Fertility and Sterility, vol. 92 No. 5, pp. 1562-1568 (Year: 2009).*
Deb et al., "Quantitative analysis of antral follicle number and size: a comparison of two-dimensional and automated three-dimensional ultrasound techniques", 2010, Ultrasound Obstetric Gynecology, pp. 354-360 (Year: 2010).*
Broekmans et al., "The antral follicle count: practical recommendations for better standardization", Aug. 2010, Fertility and Sterility, vol. 94 No. 3, pp. 1044-1051 (Year: 2010).*
Communication dated Feb. 25, 2021 issued by the European Intellectual Property Office in counterpart European Application No. 20193740.6.

* cited by examiner

ULTRASOUND DIAGNOSIS APPARATUS AND OPERATING METHOD FOR THE SAME

CROSS-REFERENCE TO RELATED APPLICATION(S)

This application is based on and claims priority under 35 U.S.C. § 119 to Korean Patent Application No. 10-2020-0006748, filed on Jan. 17, 2020, in the Korean Intellectual Property Office, the disclosure of which is incorporated by reference herein in its entirety.

BACKGROUND

1. Field

Various embodiments relate to ultrasound diagnosis apparatuses and operating methods for the same, and more particularly, to ultrasound diagnosis apparatuses and operating methods for acquiring size information regarding at least one entity included in an object based on a plurality of two-dimensional (2D) ultrasound images acquired as a probe scans the object.

2. Description of Related Art

Recently, in the medical field, various types of medical imaging apparatuses have been widely used to visualize and acquire information about living tissue of a human body for early diagnosis or surgery with regard to various diseases. Representative examples of these medical imaging apparatuses may include an ultrasound diagnosis apparatus, a computed tomography (CT) apparatus, and a magnetic resonance imaging (MRI) apparatus.

Ultrasound diagnosis apparatuses transmit ultrasound signals generated by transducers of a probe to an object and receive information of echo signals reflected from the object, thereby obtaining an image of an internal part of the object. In particular, ultrasound diagnosis apparatuses are used for medical purposes including observing an internal area of an object, detecting foreign substances, and assessing injuries. Such ultrasound diagnosis apparatuses exhibit high stability, display images in real time, and are safe due to lack of radiation exposure, as compared to diagnostic X-ray apparatuses, and therefore, ultrasound diagnosis apparatuses have been widely used together with other types of imaging diagnostic apparatuses.

Moreover, when an object is scanned using a three-dimensional (3D) probe having transducers arranged in two dimensions (2D), it is possible to measure the entire volume of the object, thereby accurately and easily obtaining a size of an entity included in the object. However, 3D probes are expensive, are heavy, meaning they are not easy to use, and inconvenience users because used probes need to be replaced.

SUMMARY

Provided are ultrasound diagnosis apparatuses and operating methods for the same, which are capable of acquiring a plurality of ultrasound images of an object by scanning the object via a two-dimensional (2D) probe having transducers arranged in one dimension (1D) and easily and accurately acquiring, based on the acquired ultrasound images, size information regarding at least one entity included in the object.

Additional aspects will be set forth in part in the description which follows and, in part, will be apparent from the description, or may be learned by practice of the presented embodiments of the disclosure.

In accordance with an aspect of the disclosure, an ultrasound diagnosis apparatus includes: a display; a memory storing one or more instructions; and a processor configured to execute the one or more instructions stored in the memory to: generate a plurality of ultrasound images of an object including a plurality of entities, based on echo signals received from the object; detect first and second entities among the plurality of entities in each of the plurality of ultrasound images; acquire size information regarding the detected first entity and size information regarding the detected second entity from each of the plurality of ultrasound images; and control the display to display, based on the size information regarding the first entity and the size information regarding the second entity, a first ultrasound image showing a largest size of the first entity and a second ultrasound image showing a largest size of the second entity, from among the plurality of ultrasound images.

The ultrasound diagnosis apparatus may further include a probe configured to transmit ultrasound signals to the object and receive the echo signals from the object, and the probe may be a two-dimensional probe having a plurality of transducers arranged in one dimension.

The plurality of ultrasound images may be consecutive ultrasound images generated based on the echo signals acquired as the probe scans the object along a first direction, and correspond to cross-sections perpendicular to the first direction.

The processor may be further configured to execute the one or more instructions to detect the first and second entities in each of the plurality of ultrasound images based on a position and a direction of at least one entity included in each of the plurality of ultrasound images.

The size information regarding the first entity may include at least one of a short axis length, a long axis length, an area, a radius, a diameter, and a circumference of the first entity detected in each of the plurality of ultrasound images, and the size information regarding the second entity may include at least one of a short axis length, a long axis length, an area, a radius, a diameter, and a circumference of the second entity detected in each of the plurality of ultrasound images.

The processor may be further configured to execute the one or more instructions to: detect the plurality of entities in each of the plurality of ultrasound images; acquire pieces of size information respectively regarding the plurality of entities; determine a third entity having a largest size from among the plurality of entities, based on the pieces of size information respectively regarding the plurality of entities; and control the display to display a third ultrasound image showing a largest size of the third entity from among the plurality of ultrasound images.

The processor may be further configured to execute the one or more instructions to: detect the plurality of entities and sizes thereof in each of the plurality of ultrasound images; determine, based on the sizes of the plurality of entities, ultrasound images respectively showing largest sizes of the plurality of entities as being ultrasound images respectively corresponding to the plurality of entities; and control the display to display ultrasound images corresponding to a predetermined number of entities, from among the plurality of entities, in order from largest to smallest in size.

The ultrasound diagnosis apparatus may further include a user input interface configured to receive the predetermined number.

the processor may be further configured to execute the one or more instructions to control the display to display size information regarding the first entity included in the first ultrasound image and size information regarding the second entity included in the second ultrasound image.

The object may be an ovary, and the plurality of entities may include follicles contained in the ovary.

In accordance with another aspect of the disclosure, an operating method of an ultrasound diagnosis apparatus includes: generating a plurality of ultrasound images of an object including a plurality of entities, based on echo signals received from the object; detecting first and second entities among the plurality of entities in each of the plurality of ultrasound images; acquiring size information regarding the detected first entity and size information regarding the detected second entity from each of the plurality of ultrasound images; and displaying, based on the size information regarding the first entity and the size information regarding the second entity, a first ultrasound image showing a largest size of the first entity and a second ultrasound image showing a largest size of the second entity, from among the plurality of ultrasound images.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
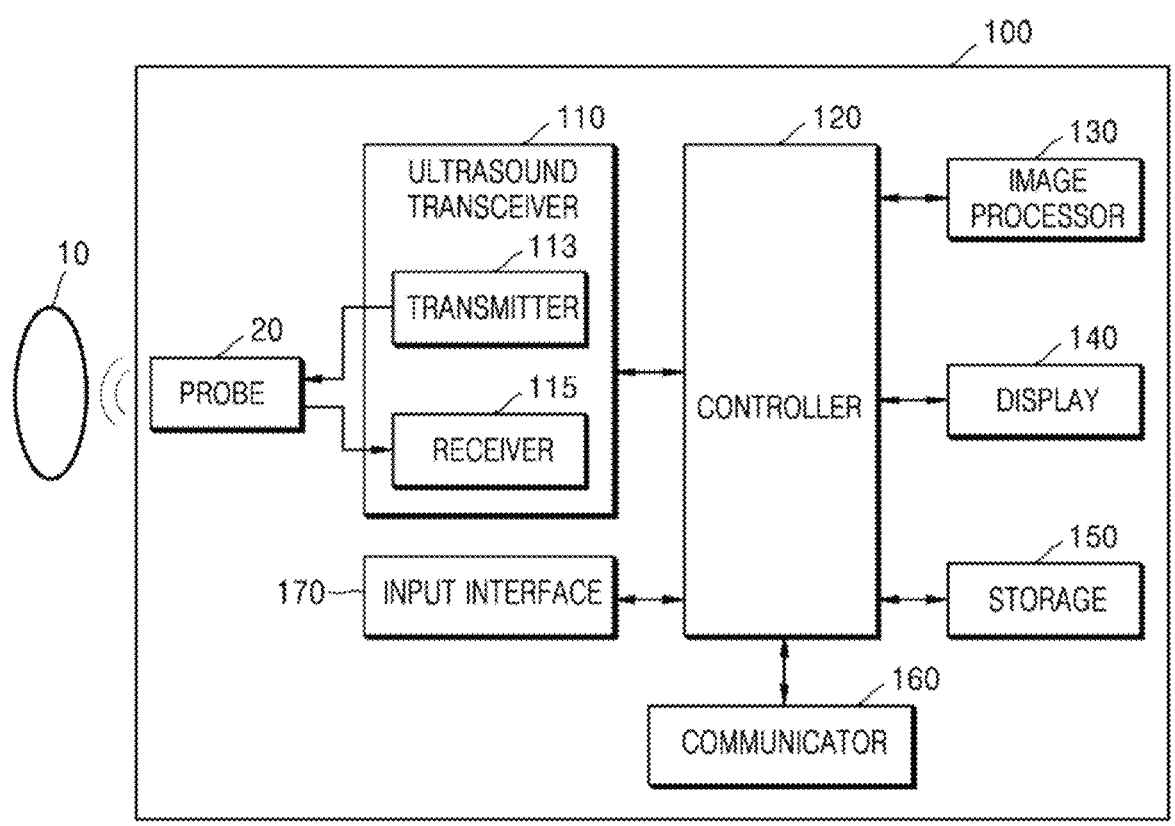
FIG. 1 is a block diagram illustrating an ultrasound diagnosis apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

As used herein, the term "and/or" includes any and all combinations of one or more of the associated listed items. Expressions such as "at least one of," when preceding a list of elements, modify the entire list of elements and do not modify the individual elements of the list.

Terms such as "part" and "portion" used herein denote those that may be embodied by software or hardware. According to exemplary embodiments, a plurality of parts or portions may be embodied by a single unit or element, or a single part or portion may include a plurality of elements.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, that is portable, moveable, mobile, or hand-held. Examples of the portable-type ultrasound diagnosis apparatus 100 may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

Figure 2C:
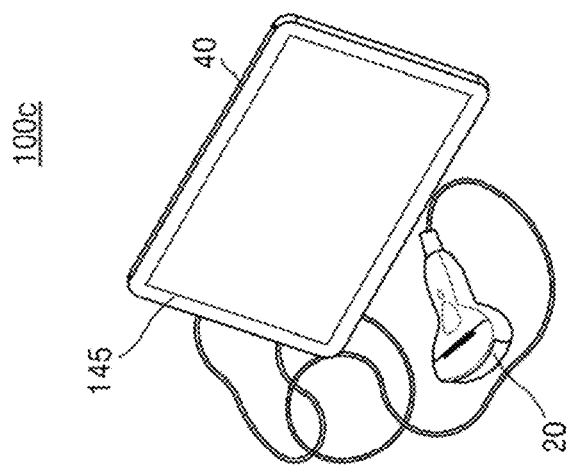
FIGS. 2A, 2B, and 2C are diagrams respectively illustrating an ultrasound diagnosis apparatus according to an exemplary embodiment.
Figure 2B:
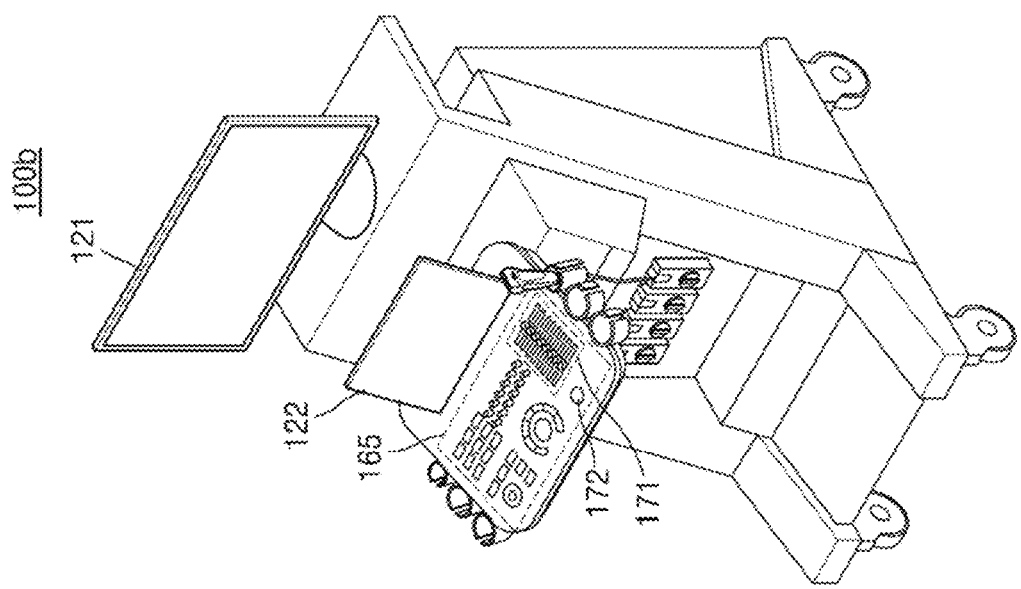
Figure 2A:
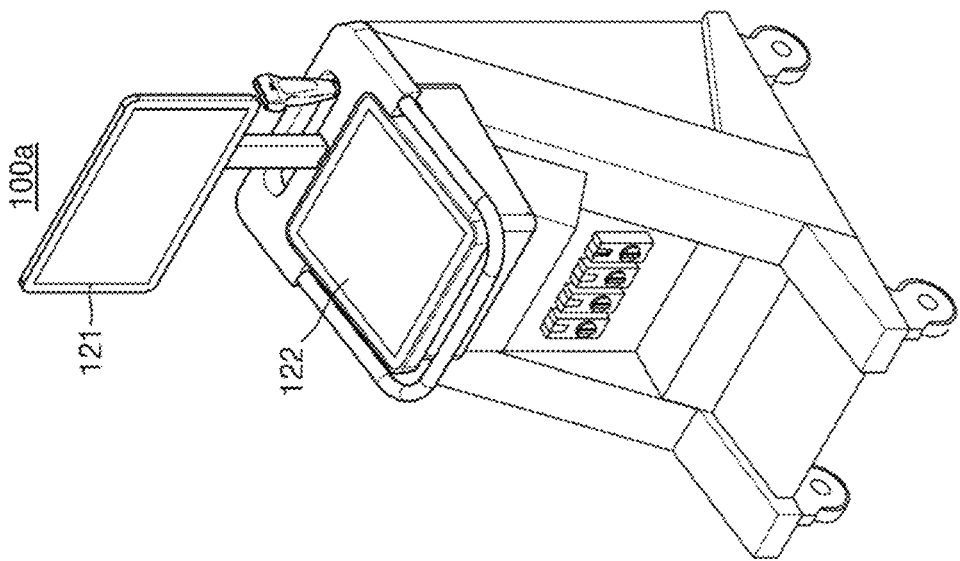

FIGS. 2A, 2B, and 2C are diagrams illustrating ultrasound diagnosis apparatus according to an exemplary embodiment.

Referring to FIGS. 2A and 2B, the ultrasound diagnosis apparatus 100 may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100. The main display 121 and the sub-display 122 may provide graphical user interfaces (GUI), thereby receiving user's inputs of data to control the ultrasound diagnosis apparatus 100. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100 may control the display of the ultrasound image on the main display 121 by using the input control data.

Referring to FIG. 2B, the ultrasound diagnosis apparatus 100 may include a control panel 165. The control panel 165 may include buttons, trackballs, jog switches, or knobs, and may receive data to control the ultrasound diagnosis apparatus 100 from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100 may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100 may include a portable device. An example of the portable ultrasound diagnosis apparatus 100 may include, for example, smart phones including probes and applications, laptop computers, personal digital assistants (PDAs), or tablet PCs, but an exemplary embodiment is not limited thereto.

The ultrasound diagnosis apparatus 100 may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100, and a GUI.

Figure 3:
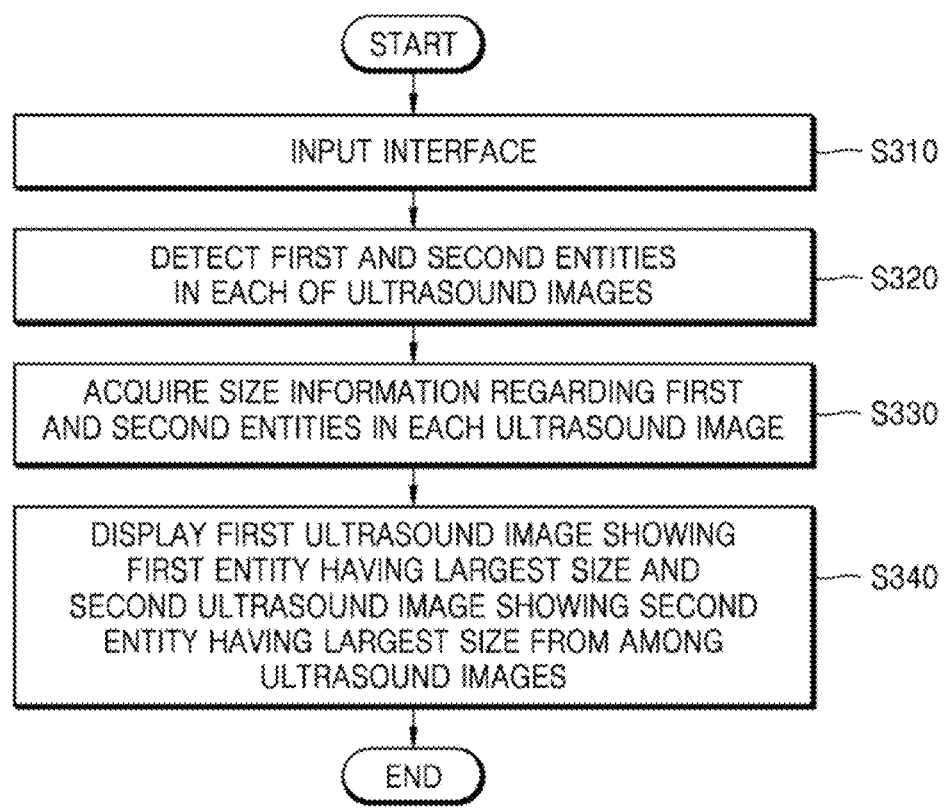
FIG. 3 is a flowchart of an operating method of an ultrasound diagnosis apparatus, according to an embodiment.

FIG. 3 is a flowchart of an operating method of the ultrasound diagnosis apparatus 100, according to an embodiment.

According to an embodiment, the ultrasound diagnosis apparatus 100 may transmit ultrasound signals to an object, acquire ultrasound data based on echo signals received from the object, and generate a plurality of ultrasound images of the object based on the ultrasound data (S310). For example, the ultrasound diagnosis apparatus 100 may acquire brightness (B)-mode data with respect to the object based on echo signals. The ultrasound diagnosis apparatus 100 may then generate a B-mode ultrasound image based on the B-mode data and display the generated B-mode ultrasound image. The ultrasound diagnosis apparatus 100 may extract B-mode components from ultrasound data and generate a B-mode ultrasound image in which signal intensities are represented as brightness based on the extracted B-mode components.

According to an embodiment, the ultrasound probe 20 for receiving echo signals from the object may be a 2D probe having a plurality of transducers arranged in 1D. Furthermore, the ultrasound diagnosis apparatus 100 may generate a plurality of consecutive ultrasound images based on echo signals acquired as the ultrasound probe 20 scans the object in a first direction. The ultrasound images may represent cross-sections of the object perpendicular to the first direction. as will be described in detail below with reference to FIG. 4.

According to an embodiment, the ultrasound diagnosis apparatus 100 may detect, in each of the ultrasound images, first and second entities from among a plurality of entities included in the object (S320).

According to an embodiment, the object may include a body part (e.g., a woman's lower abdomen) that requires examination with respect to a gynecological disease. In detail, according to an embodiment, the object may be an ovary including a plurality of follicles, but is not limited thereto. Furthermore, according to an embodiment, each of the first and second entities may include a follicle.

According to an embodiment, the ultrasound diagnosis apparatus 100 may detect the first and second entities in each of the ultrasound images by using an object tracking method or the like. For example, the ultrasound diagnosis apparatus 100 may detect a plurality of entities (e.g., follicles) included in a first ultrasound image among the ultrasound images by segmenting the first ultrasound image. The ultrasound diagnosis apparatus 100 may segment the first ultrasound image into a plurality of regions based on values of pixels in the first ultrasound image, and each of the regions may be composed of a set of pixels having pixel values in a predetermined range. Each of the regions may be a set of pixels corresponding to a follicle. The ultrasound diagnosis apparatus 100 may assign a label to each of the regions such that the regions are distinguished from one another.

Furthermore, the ultrasound diagnosis apparatus 100 may detect a plurality of entities (e.g., follicles) included in a second ultrasound image among the ultrasound images by segmenting the second ultrasound image in the same manner as for the first ultrasound image.

According to an embodiment, the ultrasound diagnosis apparatus 100 may match each of the entities detected in the first ultrasound image with a corresponding one of the entities detected in the second ultrasound image. For example, the ultrasound diagnosis apparatus 100 may identify, from among the entities detected in the second ultrasound image, the same entity as a first entity (e.g., a first follicle) among the entities detected in the first ultrasound image, based on information about a size, a position, and a direction of each of the entities detected in each of the first and second ultrasound images, a distance of each entity from another entity, and an angle of each entity relative to another entity. Furthermore, the ultrasound diagnosis apparatus 100 may identify, from among the entities detected in the second ultrasound image, the same entity as a second entity (e.g., a second follicle) among the entities detected in the first ultrasound image, based on the same information as described above.

According to an embodiment, the ultrasound diagnosis apparatus 100 may acquire pieces of size information respectively regarding the first and second entities from each of the ultrasound images (S330).

For example, the ultrasound diagnosis apparatus 100 may acquire at least one of a short axis length, a long axis length, an area, a radius, a diameter, and a circumference of the entity identified as being the first entity in each of the ultrasound images. Furthermore, the ultrasound diagnosis apparatus 100 may acquire at least one of a short axis length, a long axis length, an area, a radius, a diameter, and a circumference of the entity identified as being the second entity in each of the ultrasound images.

According to an embodiment, the ultrasound diagnosis apparatus 100 may display, based on the pieces of size information respectively regarding the first and second entities and acquired from each the ultrasound images, a first ultrasound image showing a largest size of the first entity and a second ultrasound image showing a largest size of the second entity (S340).

Furthermore, the ultrasound diagnosis apparatus 100 may display the size information regarding the first entity in the first ultrasound image and the size information regarding the second entity in the second ultrasound image.

Figure 4:
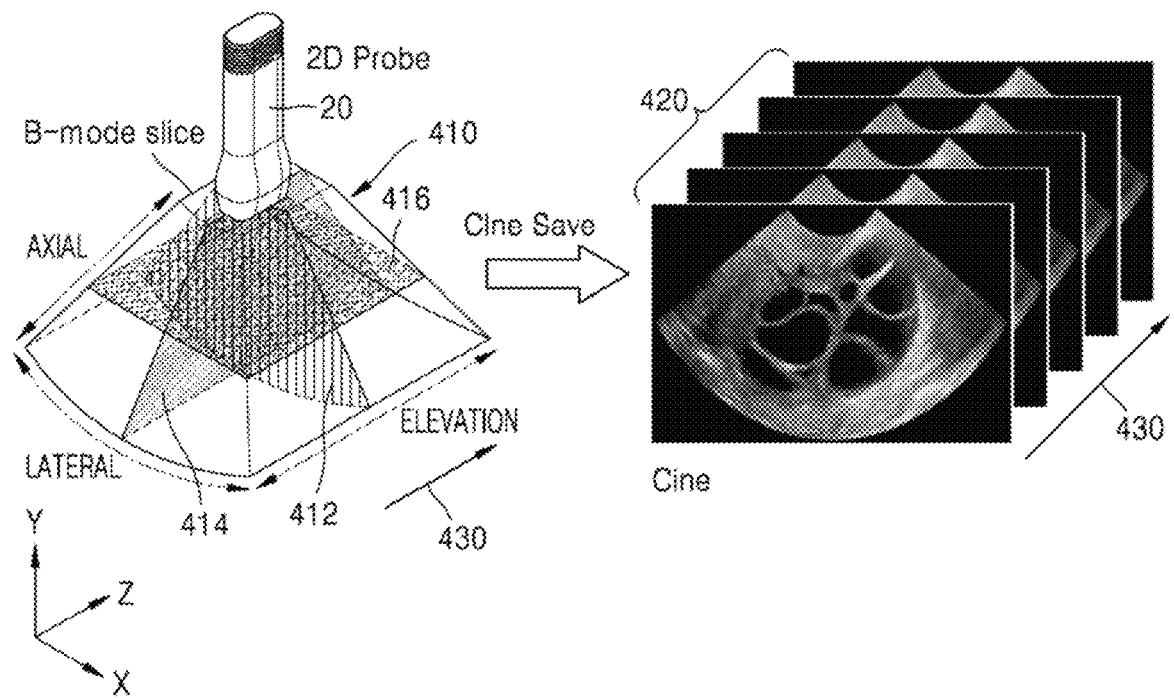
FIG. 4 is a reference diagram for describing a method by which an ultrasound diagnosis apparatus generates a plurality of ultrasound images, according to an embodiment.

FIG. 4 is a reference diagram for describing a method of generating a plurality of ultrasound images by the ultrasound diagnosis apparatus 100, according to an embodiment.

Referring to FIG. 4, according to an embodiment, the ultrasound diagnosis apparatus 100 may acquire ultrasound data by scanning an object using the ultrasound probe 20 having a plurality of transducers arranged in 1D.

As shown in FIG. 4, the ultrasound data may be represented as volume data 410. An axial direction defined in the ultrasound data indicates a propagation direction of ultrasound signals with respect to transducers of the ultrasound probe 20, a lateral direction indicates a direction of movement of a scan line, and an elevation direction indicates a depth direction, i.e., a direction of movement of the ultrasound probe 20. In other words, the volume data 410 may be generated based on echo signals acquired as the ultrasound probe 20 scans the object in a first direction (elevation direction) 430. Furthermore, the first direction 430 indicates a direction of movement of a frame (i.e., a scan plane). According to an embodiment, the ultrasound diagnosis apparatus 100 may acquire volume data with respect to an object without using a 3D probe.

Furthermore, orthogonal slices in the volume data 410 represent a slice 412 corresponding to a sagittal view, a slice 414 corresponding to a coronal view, and a slice 416 corresponding to an axial view.

According to an embodiment, the ultrasound diagnosis apparatus 100 may generate a plurality of ultrasound images 420 from the volume data 410 based on ultrasound data corresponding to slices (e.g., the sagittal view) perpendicular to the elevation direction, the ultrasound images 420 being continuously arranged in the elevation direction. Furthermore, the ultrasound diagnosis apparatus 100 may store the generated ultrasound images 420.

Figure 5:
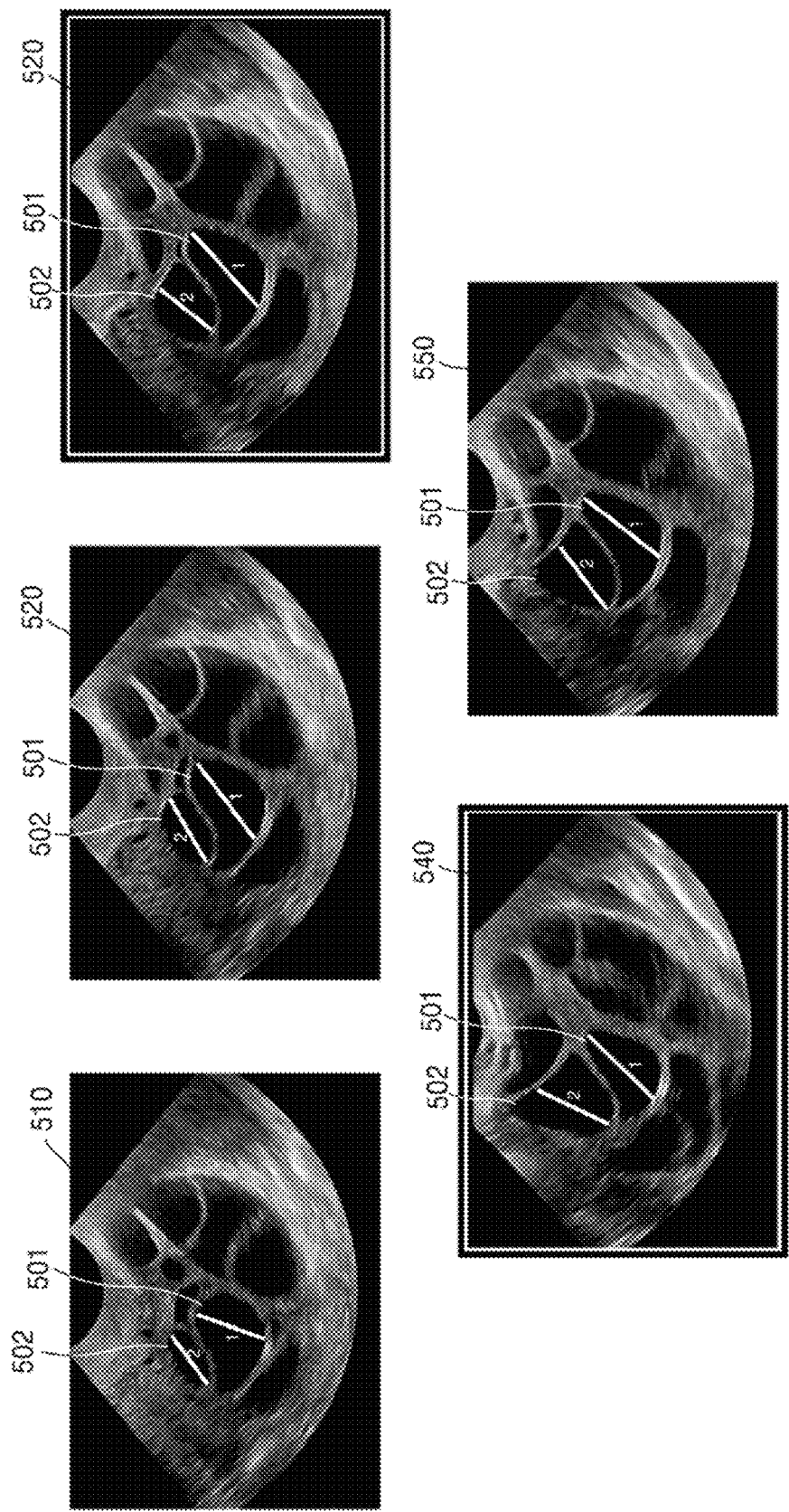
FIG. 5 is a reference diagram for describing a method by which an ultrasound diagnosis apparatus detects first and second entities in a plurality of ultrasound images, according to an embodiment.

FIG. 5 is a reference diagram for describing a method of detecting first and second entities in a plurality of ultrasound images by the ultrasound diagnosis apparatus 100, according to an embodiment.

Referring to FIG. 5, according to an embodiment, an object may include a plurality of entities. For example, according to an embodiment, the object may be an ovary including a plurality of follicles. Accordingly, each of a plurality of ultrasound images acquired by scanning the object (e.g., the ovary) may have a plurality of follicles shown therein.

According to an embodiment, the ultrasound diagnosis apparatus 100 may detect a plurality of follicles in each of a plurality of ultrasound images, i.e., first through fifth ultrasound images 510, 520, 530, 540, and 540. For example, the ultrasound diagnosis apparatus 100 may segment the first ultrasound image 510 into a plurality of regions. In this case, each of the regions may be composed of a set of pixels having pixel values in a predetermined range. Each of the regions may be a set of pixels corresponding to a follicle, and the ultrasound diagnosis apparatus 100 may identify a plurality of entities including first and second entities 501 and 502 in the first ultrasound image 510. Furthermore, according to an embodiment, the ultrasound diagnosis apparatus 100 may perform segmentation using a trained neural network.

In addition, the ultrasound diagnosis apparatus 100 may perform segmentation on the second ultrasound image 520 in the same manner as performed on the first ultrasound image 510 to detect a plurality of entities including the first and second entities 501 and 502 in the second ultrasound image 520.

According to an embodiment, the ultrasound diagnosis apparatus 100 may match each of the entities detected in the first ultrasound image 510 with a corresponding one of the entities detected in the second ultrasound image 520.

For example, the ultrasound diagnosis apparatus 100 may identify, from among the entities detected in the second ultrasound image 520, the same entity as the first entity (e.g., a first follicle) 501 among the entities detected in the first ultrasound image 510.

The ultrasound diagnosis apparatus 100 may match the first entity 501 in the first ultrasound image 510 with the first entity 501 in the second ultrasound image 520, based on pieces of information about a size, a position, and a direction of each of the entities in the first ultrasound image 510, a distance of each entity from another entity, and an angle of each entity relative to another entity and information about a size, a position, and a direction of each of the entities in the second ultrasound image 520, a distance of each entity from another entity, and an angle of each entity relative to another entity. Furthermore, the ultrasound diagnosis apparatus 100 may match the second entity 502 in the first ultrasound image 510 with the second entity 502 in the second ultrasound image 520.

Accordingly, according to an embodiment, the ultrasound diagnosis apparatus 100 may detect the first and second entities 501 and 502 in each of the first through fifth ultrasound images 510, 520, 530, 540, and 550.

According to an embodiment, when the first and second entities 501 and 502 are detected in each of the first through fifth ultrasound images 510, 520, 530, 540, and 550, the ultrasound diagnosis apparatus 100 may acquire pieces of size information respectively regarding the first and second entities 501 and 502 from each of the first through fifth ultrasound images 510, 520, 530, 540, and 550.

For example, the ultrasound diagnosis apparatus 100 may acquire at least one of a short axis length, a long axis length, an area, a radius, a diameter, and a circumference of the first entity 501 in the first ultrasound image 510 as a first piece of size information regarding the first entity 501. Furthermore, the ultrasound diagnosis apparatus 100 may acquire at least one of a short axis length, a long axis length, an area, a radius, a diameter, and a circumference of the first entity 501 in the second ultrasound image 520 as a second piece of size information regarding the first entity 501, and may acquire third through fifth pieces of size information respectively regarding the first entities 501 in the third through fifth ultrasound images 530, 540, and 550 as well.

In this case, the first through fifth pieces of size information regarding the first entity 501 may be values of the same parameter. For example, all the first through fifth pieces of size information are values for a short axis length of the first entity 501 or values for an area of the first entity 501.

The ultrasound diagnosis apparatus 100 may compare the first through fifth pieces of size information regarding the first entity 501 with one another and determine an ultrasound image (e.g., the third ultrasound image 530), in which a size (e.g., a long axis length) of the first entity 501 is shown to be largest, to be an ultrasound image corresponding to the first entity 501.

Furthermore, in the same manner as for the first entity 501, the ultrasound diagnosis apparatus 100 may acquire at least one of a short axis length, a long axis length, an area, a radius, a diameter, and a circumference of the second entity 502 in the first ultrasound image 510 as a first piece of size information regarding the second entity 502. Furthermore, the ultrasound diagnosis apparatus 100 may acquire at least one of a short axis length, a long axis length, an area, a radius, a diameter, and a circumference of the second entity 502 in the second ultrasound image 520 as a second piece of size information regarding the second entity 502, and may acquire third through fifth pieces of size information respectively regarding the second entities 502 in the third through fifth ultrasound images 530, 540, and 550 as well. In this case, the first through fifth pieces of size information regarding the second entity 502 may be values of the same parameter. Furthermore, all the first through fifth pieces of size information are values for the same parameter as the first through fifth pieces of size information regarding the first entity 501.

The ultrasound diagnosis apparatus 100 may compare the first through fifth pieces of size information regarding the second entity 502 with one another and determine an ultrasound image (e.g., the fourth ultrasound image 540), in which a size (e.g., a long axis length) of the second entity 502 is shown to be largest, to be an ultrasound image corresponding to the second entity 502.

Although FIG. 5 shows a plurality of ultrasound images as including five ultrasound images, this is for convenience of description and the ultrasound images may include a larger number of ultrasound images.

Figure 6:
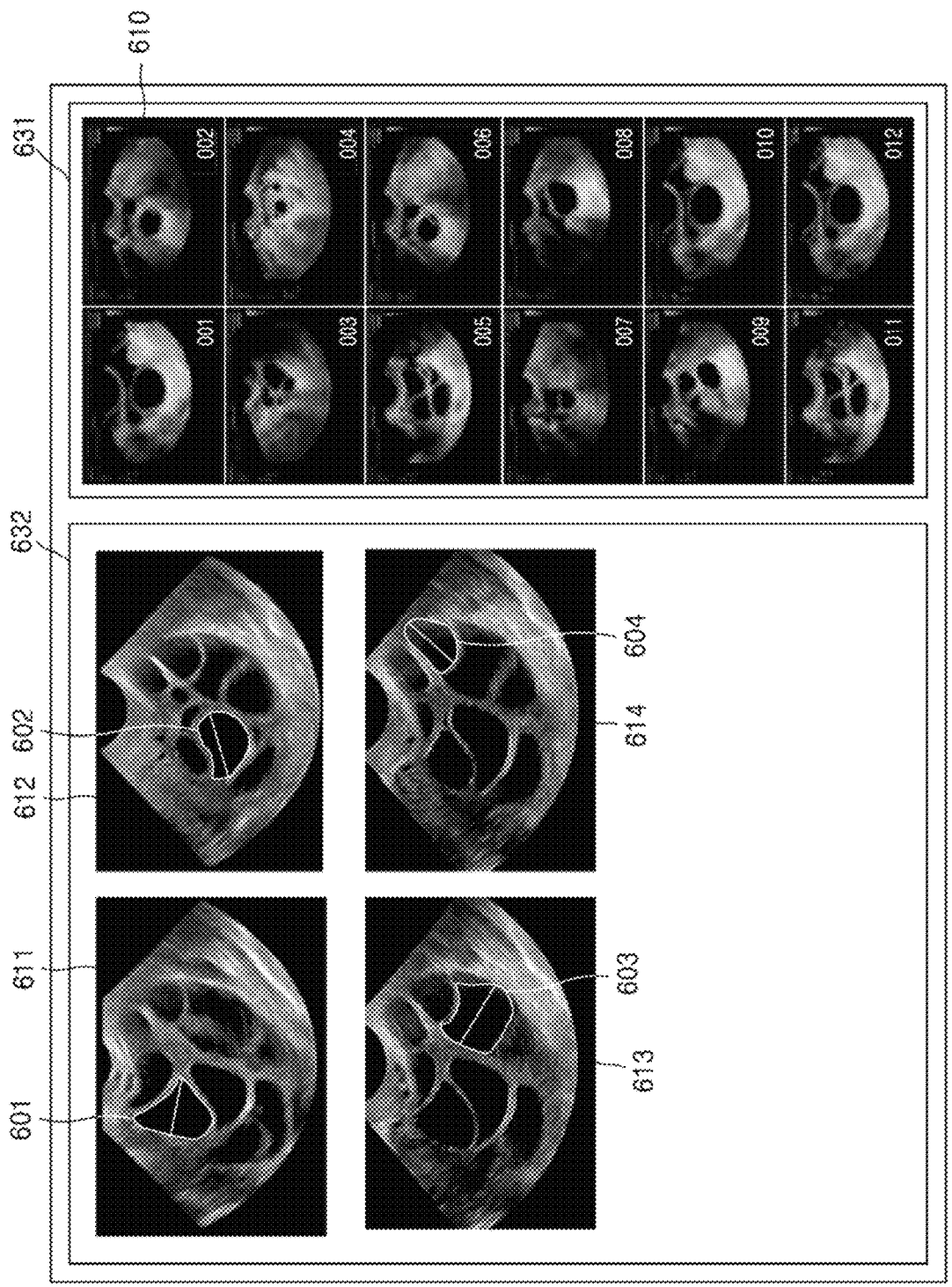
FIG. 6 illustrates an example in which an ultrasound diagnosis apparatus displays an ultrasound image based on size information regarding an entity, according to an embodiment.

FIG. 6 illustrates an example in which the ultrasound diagnosis apparatus 100 displays an ultrasound image based on size information regarding an entity, according to an embodiment.

Referring to FIG. 6, according to an embodiment, the ultrasound diagnosis apparatus 100 may display a plurality of consecutive ultrasound images 610 of an object in a first region 631 of the display 140. The ultrasound diagnosis apparatus 100 may generate the consecutive ultrasound images 610 based on echo signals acquired as the ultrasound probe 20 scans the object along a first direction, and display the generated consecutive ultrasound images 610. In this case, the consecutive ultrasound images 610 may be ultrasound images representing cross-sections of the object perpendicular to the first direction.

According to an embodiment, the object may include a plurality of entities, and each of the ultrasound images 610 may include the entities. The ultrasound diagnosis apparatus 100 may identify the entities in each of the ultrasound images 610 and acquire pieces of size information respectively regarding the entities therein. For example, when the object (e.g., an ovary) includes first through fourth entities (e.g., first through fourth follicles) 601 through 604, the ultrasound diagnosis apparatus 100 may acquire pieces of size information respectively regarding the first through fourth entities 601 through 604 in each of the ultrasound images 610. Descriptions of the method of acquiring pieces of size information regarding entities are already provided above with respect to FIG. 5, and thus, are not repeated below.

According to an embodiment, the ultrasound diagnosis apparatus 100 may display, in a second region 632 of the display 140, ultrasound images respectively showing largest sizes of the first through fourth entities 601 through 604 from among the ultrasound images 610, based on the pieces of size information respectively regarding the first through fourth entities 601 through 604.

For example, the ultrasound diagnosis apparatus 100 may display in the second region 632 a first ultrasound image 611 showing a largest size of the first entity 601 (e.g., a first follicle) from among the ultrasound images 610, based on the pieces of size information respectively regarding the first through fourth entities 601 through 604. In this case, the ultrasound diagnosis apparatus 100 may display the first entity 601 (i.e., the first follicle) included in the first ultrasound image 611 to be distinguished from the other follicles. A border of the first entity 601 that is the first follicle may be highlighted by a thick solid line. Furthermore, size information regarding the first follicle (e.g., "a long axis length: 10.5 mm") may be displayed.

Furthermore, in the same manner as for the first entity 601, the ultrasound diagnosis apparatus 100 may display in the second region 632 a second ultrasound image 612 showing a largest size of the second entity 602, i.e., the second follicle, from among the ultrasound images 610, such that the second entity 602, i.e., the second follicle, may be identified in the second ultrasound image 612, and display size information regarding the second follicle together with the second ultrasound image 612. Furthermore, the ultrasound diagnosis apparatus 100 may display, in the second region 632, a third ultrasound image 613 showing a largest size of the third entity 603 (i.e., the third follicle) from among the ultrasound images 610 and a fourth ultrasound image 614 showing a largest size of the fourth entity 604 (i.e., a fourth follicle) thereamong.

In addition, the ultrasound diagnosis apparatus 100 may display, based on the pieces of size information regarding the first through fourth entities 601 through 604 (i.e., the first through fourth follicles), the first through fourth ultrasound images 611 through 614 in order from largest to smallest in size. For example, when size decreases in the order of the first entity (follicle) 601, the fourth entity (follicle) 604, the second entity (follicle) 602, and the third entity (follicle) 603, the ultrasound diagnosis apparatus 100 may display, in the second region 632, the first ultrasound image 611, the fourth ultrasound image 614, the second ultrasound image 612, and the third ultrasound image 613 in the stated order, but is not limited thereto.

Figure 7:
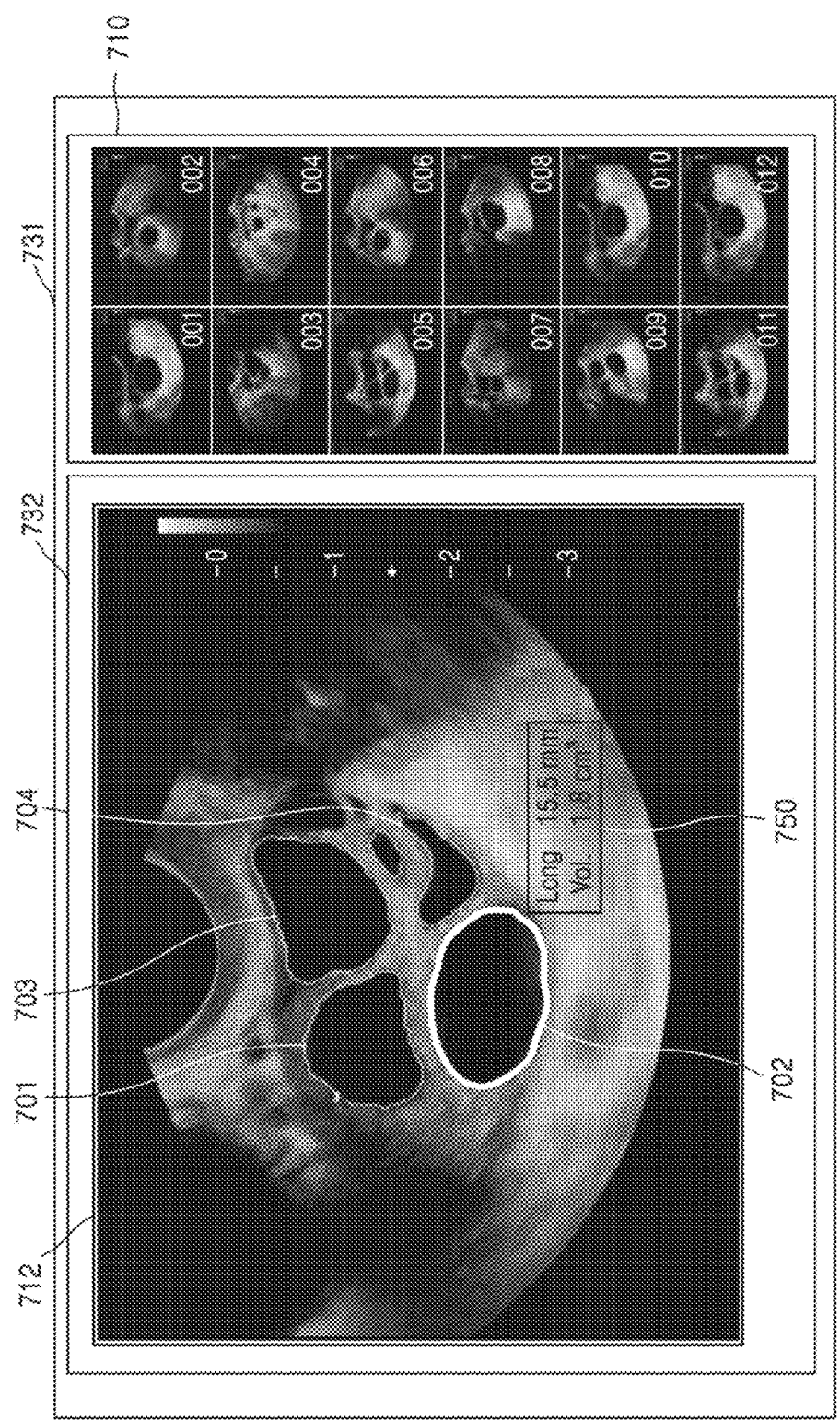
FIG. 7 illustrates an example in which an ultrasound diagnosis apparatus displays an ultrasound image based on size information regarding an entity, according to an embodiment.

FIG. 7 illustrates an example in which the ultrasound diagnosis apparatus 100 displays an ultrasound image based on size information regarding an entity, according to an embodiment.

Referring to FIG. 7, according to an embodiment, the ultrasound diagnosis apparatus 100 may display a plurality of ultrasound images 710 in a first region 731 of the display 140 and acquire pieces of size information regarding a plurality of entities in each of the ultrasound images 710. For example, when the object (e.g., an ovary) includes first through fourth entities (e.g., first through fourth follicles) 701 through 704, the ultrasound diagnosis apparatus 100 may acquire pieces of size information respectively regarding the first through fourth entities 701 through 704 in each of the ultrasound images 710. Descriptions of a method of acquiring pieces of size information regarding entities are already provided in detail above with respect to FIG. 5, and thus, are not repeated below.

An ultrasound image corresponding to an entity having a largest size from among a plurality of entities may be displayed based on pieces of size information regarding the entities.

For example, the ultrasound diagnosis apparatus 100 may determine a largest size (a first size) of the first entity 701 based on pieces of size information regarding the first entity 701, which are respectively acquired from the ultrasound images 710, a largest size (a second size) of the second entity 702 based on pieces of size information regarding the second entity 702 acquired therefrom, a largest size (a third size) of the third entity 703 based on pieces of size information regarding the third entity 703 acquired therefrom, and a largest size (a fourth size) of the fourth entity 704 based on pieces of size information regarding the fourth entity 704 acquired therefrom.

The ultrasound diagnosis apparatus 100 may determine a largest one from among the first through fourth sizes, and display an ultrasound image corresponding to the largest size in a second region 732 of the display 140. For example, when the second size is largest among the first through fourth sizes, the ultrasound diagnosis apparatus 100 may display, in the second region 732, a second ultrasound image 712 in which a size of the second entity 702 is shown to be largest. In addition, the ultrasound diagnosis apparatus 100 may display the second entity 702 to be identified in the second ultrasound image 712, together with size information 750 regarding the second entity 702.

Figure 8:
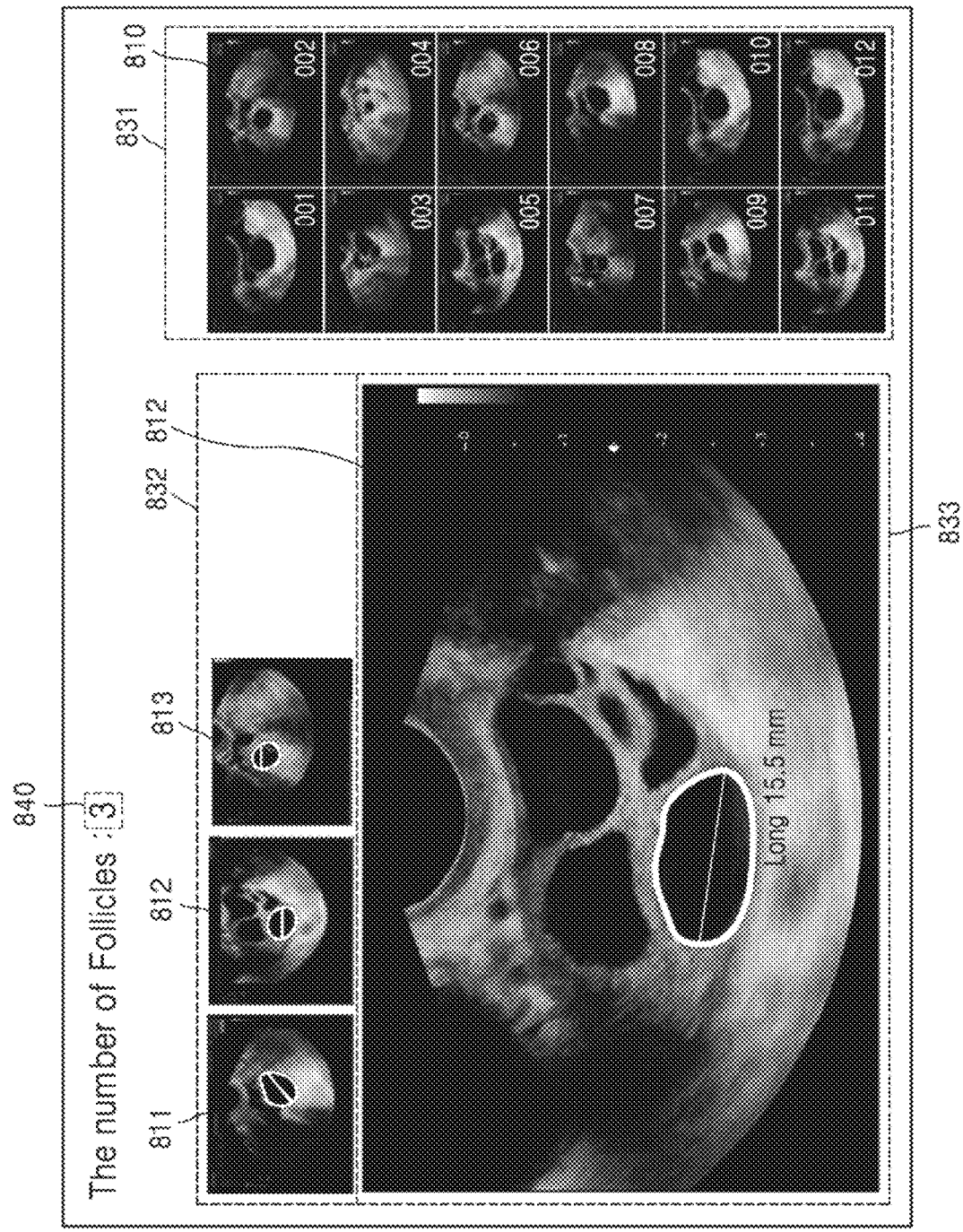
FIG. 8 illustrates an example in which an ultrasound diagnosis apparatus displays an ultrasound image based on size information regarding an entity, according to an embodiment.

FIG. 8 illustrates an example in which the ultrasound diagnosis apparatus 100 displays an ultrasound image based on size information regarding an entity, according to an embodiment.

Referring to FIG. 8, according to an embodiment, the ultrasound diagnosis apparatus 100 may display a plurality of ultrasound images 810 in a first region 831 of the display 140 and acquire pieces of size information regarding a plurality of entities. For example, when the object (e.g., an ovary) includes first through fourth entities (e.g., first through fourth follicles), the ultrasound diagnosis apparatus 100 may display pieces of size information regarding the first through fourth entities from each of the ultrasound images 810. Descriptions of the method of acquiring pieces of size information regarding entities are already provided above with respect to FIG. 5, and thus, are not repeated below.

According to an embodiment, the ultrasound diagnosis apparatus 100 may set the number 840 of entities whose size information is to be displayed from among a plurality of entities. For example, the ultrasound diagnosis apparatus 100 may receive a user input of setting the number of entities and set the number 840 of entities whose size information is to be displayed.

For example, as shown in FIG. 8, when the number 840 of entities is set to '3' based on a user input, the ultrasound diagnosis apparatus 100 may determine three (3) entities respectively having three largest sizes from among a plurality of entities included in the object and display ultrasound images respectively corresponding to the three entities and pieces of size information regarding the three entities. The ultrasound diagnosis apparatus 100 may not display all ultrasound images respectively corresponding to the first through fourth entities but display only three ultrasound images 811 through 813 respectively corresponding to three largest entities in a second region 832 of the display 140. Furthermore, the ultrasound diagnosis apparatus 100 may display an entity corresponding to each of the three ultrasound images 811 through 813 to be distinguished from other entities, and display size information regarding the entity.

In addition, the ultrasound diagnosis apparatus may enlarge and display, from among the three ultrasound images 811 through 813 displayed in the second region 833, a second ultrasound image 812 corresponding to a second entity 802 having a largest size in a third region 833.

Alternatively, when receiving a user input of selecting one of the three ultrasound images 811 through 813 displayed in the second region 832, the ultrasound diagnosis apparatus 100 may enlarge the selected ultrasound image and display it in the third region 833. However, embodiments are not limited thereto.

Figure 9:
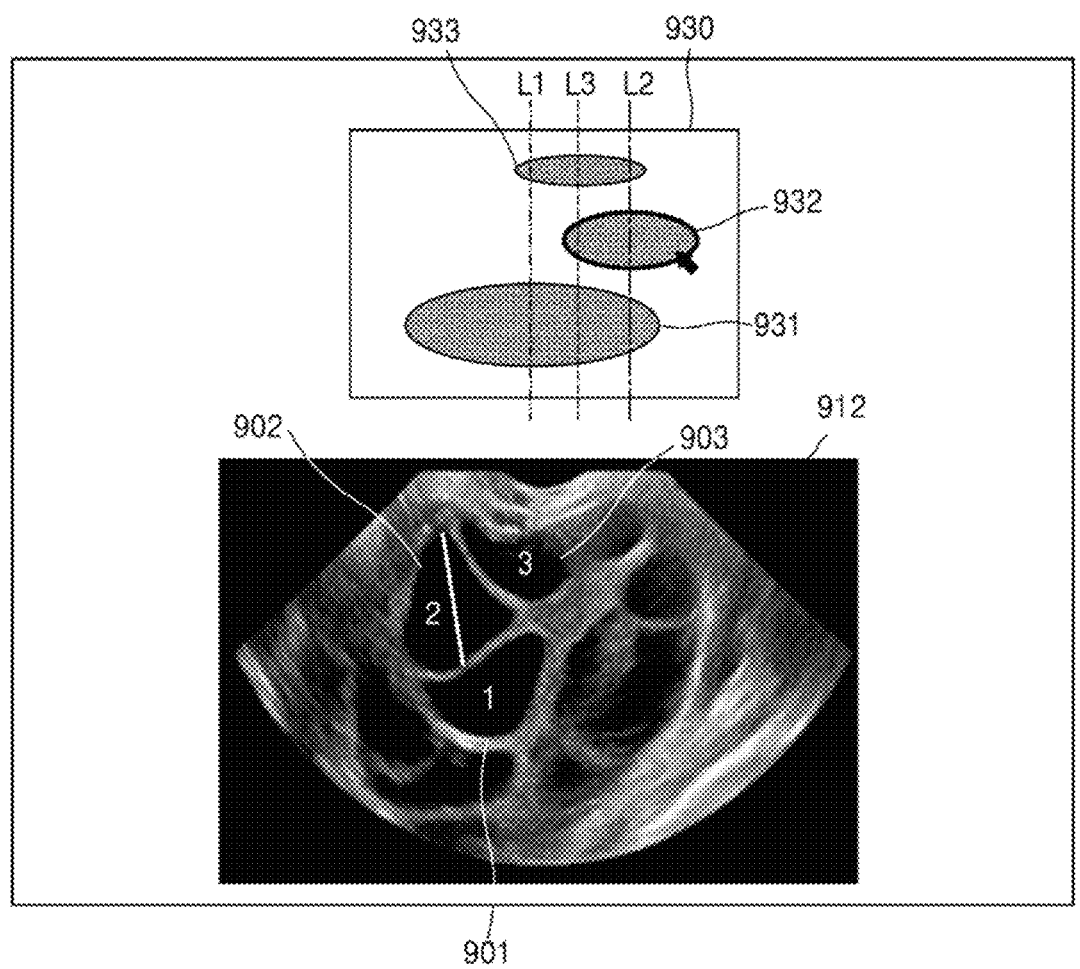
FIG. 9 illustrates an example in which an ultrasound diagnosis apparatus displays an ultrasound image based on size information regarding an entity, according to an embodiment.

FIG. 9 illustrates an example in which the ultrasound diagnosis apparatus 100 displays an ultrasound image based on size information regarding an entity, according to an embodiment.

Referring to FIG. 9, according to an embodiment, the ultrasound diagnosis apparatus 100 may acquire pieces of size information regarding a plurality of entities from each of a plurality of ultrasound images. For example, when an object (ovary) includes first through third follicles 901 through 903, the ultrasound diagnosis apparatus 100 may acquire information about at least one of a short axis length, a long axis length, an area, a radius, a diameter, and a circumference of each of the first through third follicles 901 through 903 from each of a plurality of ultrasound images. However, for convenience, an example of acquiring information about a diameter of each of the first through third follicles 901 through 903 is described with referenced to FIG. 9.

The ultrasound diagnosis apparatus 100 may display a first indicator 931 corresponding to the first follicle 901 by using pieces of information about a diameter of the first follicle 901, which are respectively acquired from the ultrasound images.

For example, as described with reference to FIG. 4, when the ultrasound images correspond to a slice (the sagittal view) perpendicular to the elevation direction (first direction), a slice 930 where a first indicator 931 is displayed may be a slice corresponding to a coronal view or an axial view. A shape of the first indicator 931 may be determined based on lengths of the diameter of the first follicle 901, which are respectively acquired from the ultrasound images. Furthermore, a second indicator 932 corresponding to the second follicle 902 may be displayed using pieces of information about a diameter of the second follicle 902, which are respectively acquired from the ultrasound images, and a shape of the second indicator 932 may be determined based on lengths of the diameter of the second follicle 902, which are respectively acquired from the ultrasound images.

In addition, a third indicator 933 corresponding to the third follicle 903 may be displayed using pieces of information about a diameter of the third follicle 903, which are respectively acquired from the ultrasound images, and a shape of the third indicator 933 may be determined based on lengths of the diameter of the third follicle 903 respectively acquired from the ultrasound images.

According to an embodiment, the ultrasound diagnosis apparatus 100 may detect, based on the ultrasound images, a relative position or size of each of the first through third follicles 901 through 903 in a sagittal view direction, and as the first through third indicators 931 through 933 are indicated on the slice 930, the user may identify the overall relative position or size of each of the first through third follicles 901 through 903 in the coronal or axial view direction.

In addition, the ultrasound diagnosis apparatus 100 may display lines, i.e., first through third lines L1 through L3, respectively indicating positions where largest lengths of diameters are measured in the first through third follicles 901 through 903. For example, the ultrasound diagnosis apparatus 100 may display the first line L1 indicating the position where a largest length of diameter is measured in the first follicle 901, the second line L2 indicating the position where a largest length of diameter is measured in the second follicle 902, and the third line L3 indicating the position where a largest length of diameter is measured in the third follicle 903.

The ultrasound diagnosis apparatus 100 may display an ultrasound image corresponding to one of the first through third lines L1 through L3. For example, when receiving a user input of selecting the second line L2 or a user input of selecting the second follicle 932, the ultrasound diagnosis apparatus 100 may display a second ultrasound image 912 in which a measured diameter of the second follicle 902 is shown to be largest from among the ultrasound images. In addition, the first through third follicles 901 through 903 may be displayed to be identified in the second ultrasound image 912, and size information regarding the second follicle 902 (e.g., the diameter of the second follicle 902) may be displayed.

Figure 10:
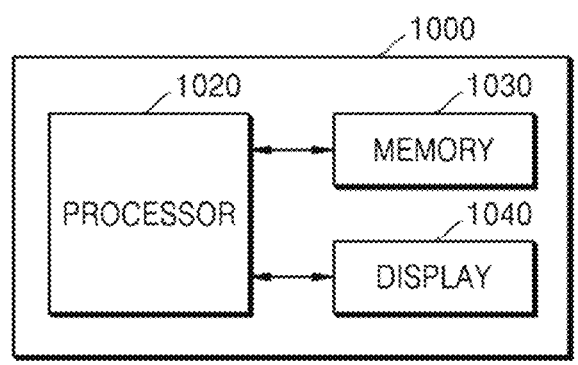
FIG. 10 is a block diagram of a configuration of an ultrasound diagnosis apparatus according to an embodiment.

FIG. 10 is a block diagram of a configuration of an ultrasound diagnosis apparatus 1000 according to an embodiment.

Referring to FIG. 10, according to an embodiment, the ultrasound diagnosis apparatus 100 may include a processor 1020, a memory 1030, and a display 1040.

The processor 1020 of FIG. 10 may correspond to at least one or a combination of the ultrasound transceiver 110, the controller 120, and the image processor 130 described with reference to FIG. 1, and the display 1040 may correspond to the display 140 of FIG. 1. Furthermore, according to an embodiment, some of the components of the ultrasound diagnosis apparatus 100 may be included in the ultrasound diagnosis apparatus 1000 of FIG. 10.

According to an embodiment, the processor 1020 may control all operations of the ultrasound diagnosis apparatus 1000. According to an embodiment, the processor 1020 may execute one or more programs stored in the memory 1030.

According to an embodiment, the memory 1030 may store various data, programs, or applications for driving and controlling the ultrasound diagnosis apparatus 1000. A program stored in the memory 1030 may include one or more instructions. Programs (one or more instructions) or applications stored in the memory 1030 may be executed by the processor 1020.

According to an embodiment, the processor 1020 may transmit ultrasound signals to an object, acquire ultrasound data based on echo signals received from the object, and generate a plurality of ultrasound images of the object based on the ultrasound data. In this case, an ultrasound probe for receiving echo signals from the object may be a 2D probe having a plurality of transducers arranged in 1D. Furthermore, the ultrasound diagnosis apparatus 1000 may generate a plurality of consecutive ultrasound images based on echo signals acquired as the ultrasound probe scans the object along a first direction. The ultrasound images may be ultrasound images representing cross-sections of the object perpendicular to the first direction.

The processor 1020 may detect a plurality of entities included in the object in each of the ultrasound images.

For example, the processor 1020 may detect a plurality of entities in each of the ultrasound images by using an object tracking method or the like. The processor 1020 may segment a first ultrasound image among the ultrasound images to detect a plurality of entities (e.g., follicles) included in the first ultrasound image. Furthermore, the processor 1020 may segment a second ultrasound image to detect entities (e.g., follicles) included in the second ultrasound image. According to an embodiment, the processor 1020 may match each of the entities detected in the first ultrasound image with a corresponding one of the entities detected in the second ultrasound image, based on information about a size, a position, and a direction of each of the entities detected in each of the first and second ultrasound images, a distance of each entity from another entity, and an angle of each entity relative to another entity.

The processor 1020 may acquire pieces of size information respectively regarding the entities from each of the ultrasound images. For example, the ultrasound diagnosis apparatus 100 may acquire at least one of a short axis length, a long axis length, an area, a radius, a diameter, and a circumference of an entity identified as being a first entity in each of the ultrasound images. Furthermore, the processor 1020 may acquire at least one of a short axis length, a long axis length, an area, a radius, a diameter, and a circumference of an entity identified as being a second entity in each of the ultrasound images.

The processor 1020 may control, based on pieces of size information respectively regarding the first and second entities and acquired from each the ultrasound images, the display 1040 to display the first ultrasound image showing a largest size of the first entity and a second ultrasound image showing a largest size of the second entity.

According to an embodiment, the display 1040 may display an operation state of the ultrasound diagnosis apparatus 1000, an ultrasound image, a user interface, etc. The display 1040 may include one or more display panels according to embodiments and may be formed as a touch screen.

According to an embodiment, the display 1040 may display the first ultrasound image showing a largest size of the first entity and a second ultrasound image showing a largest size of the second entity, and display size information regarding the first entity in the first ultrasound image and size information regarding the second entity in the second ultrasound image.

Block diagrams of the ultrasound diagnosis apparatuses 100 and 1000 of FIGS. 1 and 10 may be provided for illustration of embodiments. Each of the components in the block diagram may be integrated, added, or omitted according to the specification of the ultrasound diagnosis apparatus 100 or 1100 that is actually implemented. In other words, two or more components may be combined into a single component, or a single component may be split into two or more components if necessary. Functions performed in each block are intended to describe embodiments, and a specific operation or apparatus related to the functions does not limit the scope of the disclosure.

Methods of operating an ultrasound diagnosis apparatus may be implemented in the form of program instructions that may be performed by various types of computers and may be recorded on computer-readable recording medium. The computer-readable recording media may include program instructions, data files, data structures, etc. either alone or in combination. The program instructions recorded on the computer-readable recording media may be designed and configured specially for the disclosure or may be known to and be usable by those skilled in the art of computer software. Examples of the computer-readable recording media include magnetic media such as hard disks, floppy disks, and magnetic tape, optical media such as compact disk read-only memory (CD-ROM) and digital versatile disks (DVDs), magneto-optical media such as floptical disks, and hardware devices that are specially configured to store and perform program instructions, such as ROM, random access memory (RAM), flash memory, etc. Examples of program instructions include not only machine code such as that created by a compiler but also higher level language code that may be executed by a computer using an interpreter or the like.

In addition, ultrasound diagnostic apparatuses and operating methods for the same according to embodiments of the disclosure may be included in a computer program product when provided. The computer program product may be traded, as a commodity, between a seller and a buyer.

The computer program product may include a software program and a computer-readable storage medium having stored thereon the software program. For example, the computer program product may include a product (e.g. a downloadable application) in the form of a software program electronically distributed by a manufacturer of an ultrasound diagnostic apparatus or through an electronic market (e.g., Google Play Store™ and App Store™). For such electronic distribution, at least a part of the software program may be stored on the storage medium or may be temporarily generated. In this case, the storage medium may be a storage medium of a server of the manufacturer, a server of the electronic market, or a relay server for temporarily storing the software program.

In a system consisting of a server and a client device, the computer program product may include a storage medium of the server or a storage medium of the client device. Alternatively, in a case where a third device (e.g., a smartphone) is connected to the server or client device through a communication network, the computer program product may include a storage medium of the third device. Alternatively, the computer program product may include a software program itself that is transmitted from the server to the client device or the third device or that is transmitted from the third device to the client device.

In this case, one of the server, the client device, and the third device may execute the computer program product to perform methods according to embodiments of the disclosure. Alternatively, two or more of the server, the client device, and the third device may execute the computer program product to perform the methods according to the embodiments in a distributed manner.

For example, the server (e.g., a cloud server, an artificial intelligence server, or the like) may run the computer program product stored therein to control the client device communicating with the server to perform the methods according to the embodiments of the disclosure.

According to an embodiment, size information regarding an entity included in an object may be acquired easily and accurately without using a 3D probe.

According to an embodiment, size information regarding an entity included in the object may be acquired in consideration of the overall volume of the object without using a 3D probe.

According to an embodiment, an ultrasound diagnostic apparatus is configured to detect at least one entity included in the object and display an ultrasound image showing a largest size of the detected entity, thereby eliminating the need for the user to individually measure and remember a size of at least one entity included in the object in each of a plurality of 2D ultrasound images.

While one or more embodiments have been particularly described with reference to the figures, it will be understood by those of ordinary skill in the art that the embodiments are not to be construed as limiting the scope of the disclosure and various changes and modifications in form and details based on the basic concept of the disclosure also fall within the scope as defined by the following claims.

What is claimed is:

1. An ultrasound diagnosis apparatus comprising:
a display;
a memory storing one or more instructions; and
a processor configured to execute the one or more instructions stored in the memory, wherein the processor is configured to:
generate a plurality of ultrasound images of an object including a plurality of entities, based on echo signals received from the object;
segment each of the plurality of ultrasound images into a plurality of regions based on pixel values of each of the plurality of regions, wherein the plurality of regions correspond to the plurality of entities, respectively,
detect a first entity and a second entity which is different from the first entity among the plurality of regions in each of the plurality of ultrasound images based on the pixel values of each of the plurality of regions, wherein pixel values of the first entity and the second entity correspond to a predetermined pixel value range;
match the first entities respectively included in the plurality of ultrasound images with each other based on a direction and a position in which the first entity occupies in each ultrasound image;
match the second entities respectively included in the plurality of ultrasound images with each other based on a direction and a position in which the second entity occupies in each ultrasound image;
acquire information regarding a size of the first entity and a size of the second entity from each of the plurality of ultrasound images based on the predetermined pixel value range; and
control the display to display, based on the information regarding the size of the first entity and the size of the second entity, a first ultrasound image in which the size of the first entity is shown to be the largest from among the plurality of ultrasound images and a second ultrasound image in which the size of the second entity is shown to be the largest from among the plurality of ultrasound images,
wherein the first ultrasound image and the second ultrasound image are displayed simultaneously,
wherein the plurality of ultrasound images are consecutive ultrasound images generated based on the echo signals acquired as a probe scans the object in a single continuous sweep along a first direction, and correspond to cross-sections perpendicular to the first direction,
wherein the first ultrasound image and the second ultrasound image are acquired as the probe, which is a two-dimensional probe having a plurality of transducers arranged in one dimension, scans the object in the single continuous sweep along the first direction so that the first ultrasound image and the second ultrasound image are perpendicular to the first direction, and
wherein each of the first entity and the second entity includes follicles contained in an ovary.

2. The ultrasound diagnosis apparatus of claim 1, further comprising the probe configured to transmit ultrasound signals to the object and receive the echo signals from the object.

3. The ultrasound diagnosis apparatus of claim 1, wherein the information regarding the size of the first entity includes at least one of a short axis length, a long axis length, an area, a radius, a diameter, and a circumference of the first entity detected in each of the plurality of ultrasound images, and
the information regarding the size of the second entity includes at least one of a short axis length, a long axis length, an area, a radius, a diameter, and a circumference of the second entity detected in each of the plurality of ultrasound images.

4. The ultrasound diagnosis apparatus of claim 1, wherein the processor is further configured to:
detect the plurality of entities in each of the plurality of ultrasound images;
acquire pieces of information respectively regarding sizes of the plurality of entities;
determine a third entity having a largest size from among the plurality of entities, based on the pieces of the information respectively regarding the sizes of the plurality of entities; and
control the display to display a third ultrasound image showing the largest size of the third entity from among the plurality of ultrasound images.

5. The ultrasound diagnosis apparatus of claim 1, wherein the processor is further configured to:
detect the plurality of entities and sizes thereof in each of the plurality of ultrasound images;
determine, based on the sizes of the plurality of entities, ultrasound images respectively showing largest sizes of the plurality of entities as being ultrasound images respectively corresponding to the plurality of entities; and
control the display to display ultrasound images corresponding to a predetermined number of entities, from among the plurality of entities, in order from largest to smallest in size.

6. The ultrasound diagnosis apparatus of claim 5, further comprising a user input interface configured to receive the predetermined number.

7. The ultrasound diagnosis apparatus of claim 1, wherein the processor is further configured to control the display to display the information regarding the size of the first entity included in the first ultrasound image and the information regarding the size of the second entity included in the second ultrasound image.

8. The ultrasound diagnosis apparatus of claim 1, wherein the object is the ovary, and
the plurality of entities include follicles contained in the ovary.

9. An operating method of an ultrasound diagnosis apparatus, the operating method comprising:

generating, by a processor of the ultrasound diagnosis apparatus, a plurality of ultrasound images of an object including a plurality of entities, based on echo signals received from the object;

segmenting each of the plurality of ultrasound images into a plurality of regions based on pixel values of each of the plurality of regions, detecting, by the processor, a first entity and a second entity which is different from the first entity among the plurality of regions in each of the plurality of ultrasound images based on the pixel values of each of the plurality of regions, wherein pixel values of the first entity and the second entity correspond to a predetermined pixel value range;

matching the first entities respectively included in the plurality of ultrasound images with each other based on a direction and a position in which the first entity occupies in each ultrasound image;

matching the second entities respectively included in the plurality of ultrasound images with each other based on a direction and a position in which the second entity occupies in each ultrasound image; acquiring, by the processor, information regarding a size of the first entity and information regarding a size of the second entity from each of the plurality of ultrasound images based on the predetermined pixel value range; and displaying, based on the information regarding the size of the first entity and the information regarding the size of the second entity, a first ultrasound image in which the size of the first entity is shown to be the largest from among the plurality of ultrasound images and a second ultrasound image in which the size of the second entity is shown to be the largest from among the plurality of ultrasound images, wherein the first ultrasound image and the second ultrasound image are displayed simultaneously, wherein the plurality of ultrasound images are consecutive ultrasound images generated based on the echo signals acquired as a probe scans the object in a single continuous sweep along a first direction, and correspond to cross-sections perpendicular to the first direction, wherein the first ultrasound image and the second ultrasound image are acquired as the probe, which is a two-dimensional probe having a plurality of transducers arranged in one dimension, scans the object in the single continuous sweep along the first direction so that the first ultrasound image and the second ultrasound image are perpendicular to the first direction, and wherein each of the first entity and the second entity includes follicles contained in an ovary.

10. The operating method of claim 9, further comprising transmitting ultrasound signals to the object and receiving the echo signals from the object by using the probe.

11. The operating method of claim 9, wherein the information regarding the size of the first entity includes at least one of a short axis length, a long axis length, an area, a radius, a diameter, and a circumference of the first entity detected in each of the plurality of ultrasound images, and the information regarding the size of the second entity includes at least one of a short axis length, a long axis length, an area, a radius, a diameter, and a circumference of the second entity detected in each of the plurality of ultrasound images.

12. The operating method of claim 9, further comprising:

detecting the plurality of entities in each of the plurality of ultrasound images;

acquiring pieces of the information respectively regarding sizes of the plurality of entities;

determining a third entity having a largest size from among the plurality of entities, based on the pieces of the information respectively regarding the sizes of the plurality of entities; and displaying a third ultrasound image showing the largest size of the third entity from among the plurality of ultrasound images.

13. The operating method of claim 9, further comprising:

detecting the plurality of entities and the sizes thereof in each of the plurality of ultrasound images;

determining, based on the sizes of the plurality of entities, ultrasound images respectively showing largest sizes of the plurality of entities as being ultrasound images respectively corresponding to the plurality of entities; and displaying ultrasound images corresponding to a predetermined number of entities, from among the plurality of entities, in order from largest to smallest in size.

14. The operating method of claim 13, further comprising receiving the predetermined number via a user input interface.

15. The operating method of claim 9, further comprising displaying the information regarding the size of the first entity included in the first ultrasound image and the information regarding the size of the second entity included in the second ultrasound image.

16. The operating method of claim 9, wherein the object is the ovary, and the plurality of entities include the follicles contained in the ovary.

17. A non-transitory computer-readable recording medium having recorded thereon a program for executing in a computer the operating method of claim 9.

* * * * *